US00PP28283P3

(12) United States Plant Patent
Tan

(10) Patent No.: US PP28,283 P3
(45) Date of Patent: Aug. 15, 2017

(54) ***HIBISCUS* PLANT NAMED 'TAHI12'**

(50) Latin Name: *Hibiscus×moscheutos*
Varietal Denomination: TAHI12

(71) Applicant: Alain Tan, Montauban (FR)

(72) Inventor: Alain Tan, Montauban (FR)

( * ) Notice: Subject to any disclaimer, the term of this patent is extended or adjusted under 35 U.S.C. 154(b) by 21 days.

(21) Appl. No.: 14/757,369

(22) Filed: Dec. 22, 2015

(65) Prior Publication Data

US 2017/0094860 P1 Mar. 30, 2017

(30) Foreign Application Priority Data

Sep. 29, 2015 (QZ) ..... PBR 2015/2258

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Penny J. Aguirre

(57) ABSTRACT

A new cultivar of *Hibiscus* plant named 'TAHI12' that is characterized by its upright and well-branched plant habit, its large flowers that are light pink in color with veins and an eye-zone that is dark purple-red and its foliage that is green and suffused with dark purple.

2 Drawing Sheets

Botanical classification: *Hibiscus×moscheutos*.
Cultivar designation: 'TAHI12'.

CROSS REFERENCE TO RELATED APPLICATIONS

This application is co-pending with U.S. Plant Patent Applications filed for 2 plants derived from the same breeding program that are entitled *Hibiscus* Plant Named 'TAHI16' (U.S. Plant patent application Ser. No. 14/757,377) and *Hibiscus* Plant Named 'TAHI56' (U.S. Plant patent application Ser. No. 14/757,358).

BACKGROUND OF THE INVENTION

The present invention relates to a new and distinct cultivar of *Hibiscus* plant botanically known as *Hibiscus×moscheutos* 'TAHI12' and will be referred to hereafter by its cultivar name, 'TAHI12'. 'TAHI12' is a new cultivar of hardy *hibiscus* grown for use as a container and landscape plant.

The new cultivar was developed through an on-going breeding program conducted by the Inventor in Montauban, France. The new cultivar arose from a cross made in September of 2010 between *Hibiscus* 'Summer Storm' (U.S. Plant Pat. No. 20,443) as the female parent and *Hibiscus×moscheutos* 'Griotte' (not patented) as the male parent. 'TAHI12' was selected as a single unique plant in September of 2012 from the resulting seedlings of the above cross.

Asexual propagation of the new cultivar was first accomplished by softwood stem cuttings in Montauban, France in 2012 by the Inventor. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics of 'TAHI12'. These attributes in combination distinguish 'TAHI12' as a new and distinct cultivar of *Hibiscus*.

1. 'TAHI12' exhibits an upright, well-branched plant habit.
2. 'TAHI12' exhibits flowers that are light pink in color with veins and an eye-zone that is dark purple-red.
3. 'TAHI12' exhibits large flowers that grow up to 25 cm in diameter.
4. 'TAHI12' exhibits foliage that is green and suffused with dark purple.

The female parent plant, 'Summer Storm', is similar to 'TAHI12' in having flowers that are pink in color. 'Summer Storm' differs from 'TAHI12' in having flowers that are slightly smaller in diameter and darker pink in color with less over overlapping of the petals. The male parent plant, 'Griotte', is similar to 'TAHI12' in having an upright plant habit. 'Griotte' differs from 'TAHI12' in having flowers that are cherry red in color. 'TAHI12' can also be compared to the cultivar 'Kopper King' (U.S. Plant Pat. No. 10,793) and cultivars that derived from the same breeding program; 'TAHI16' and 'TAHI56'. 'Kopper King' differs from 'TAHI12' in having a taller plant height and in flowers that are white in color. 'TAHI16' differs from 'TAHI12' in having red flowers. 'TAHI56' differs from 'TAHI12' in having flowers that are very pale purple-white in color.

BRIEF DESCRIPTION OF THE DRAWINGS

The accompanying colored photographs illustrates the overall appearance and distinct characteristics of the new *Hibiscus*. The photographs were taken of a twelve month-old plant of 'TAHI12' as grown in a 23-cm container in an un-heated greenhouse in Boskoop, The Netherlands.

The photograph in FIG. 1 provides a side view of 'TAHI12' in bloom.

Figure 1:
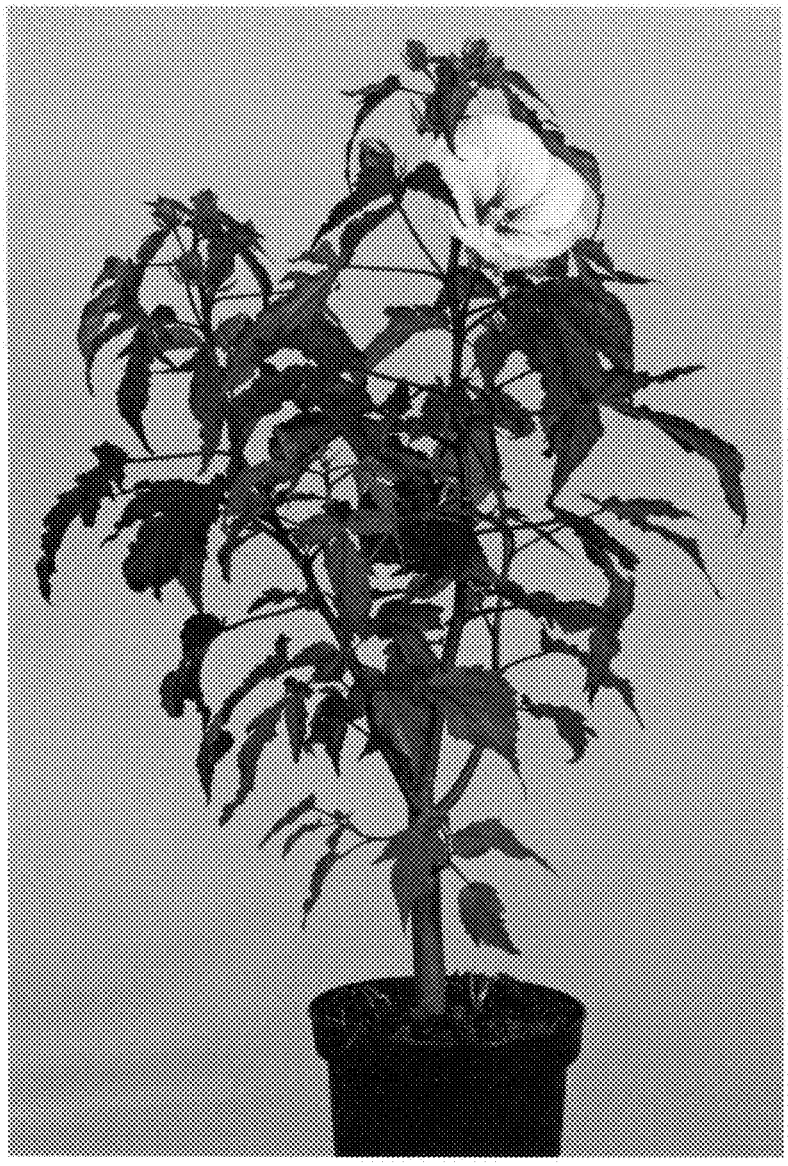
Figure 2:
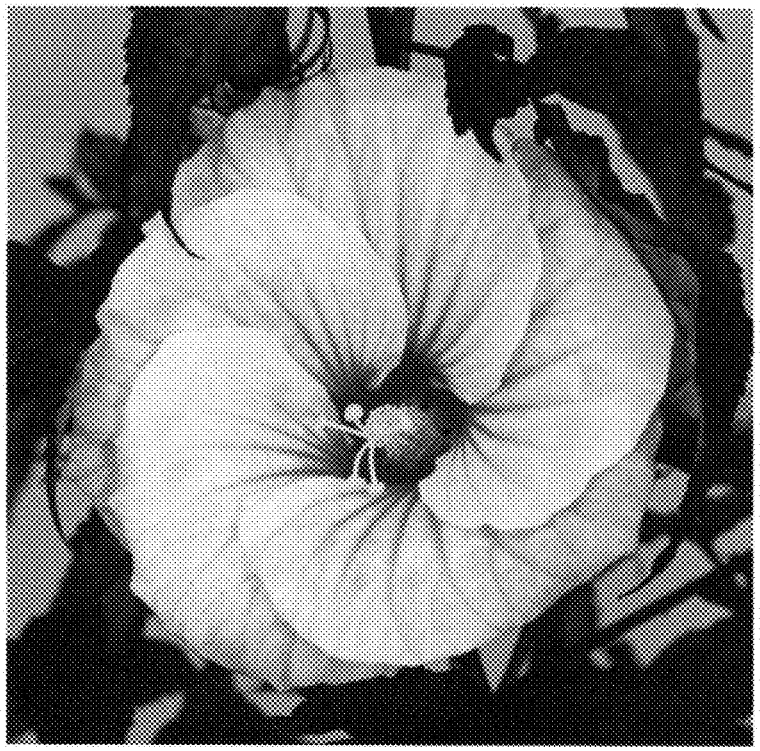

The photograph in FIG. 2 provides a close-up view of a flower of 'TAHI12'.

Figure 3:
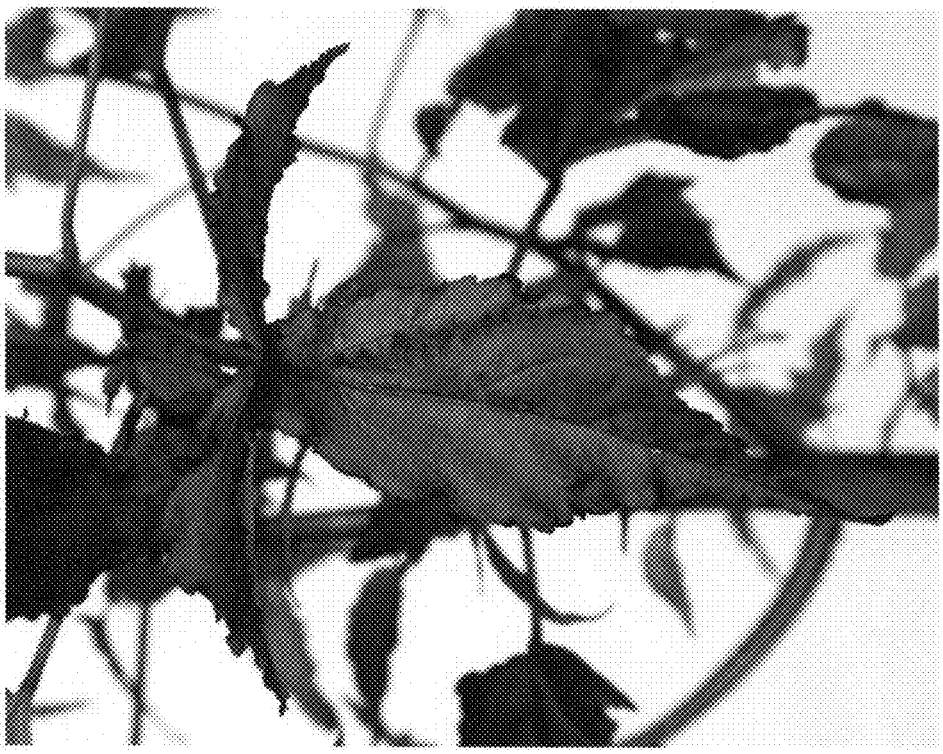

The photograph in FIG. 3 provides a close-up view of a leaf of 'TAHI12'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 12 month-old plants of the new cultivar as grown outdoors in 23-cm container in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—Late summer to beginning of Autumn in The Netherlands.

*Plant type.*—Herbaceous perennial.

*Plant habit.*—Upright, well-branched.

*Height and spread.*—Reaches about 79.7 cm in height and 55 cm in spread.

*Cold hardiness.*—At least in U.S.D.A. Zone 5.

*Diseases and pests.*—No susceptibility or resistance to diseases or pests has been observed.

*Root description.*—Fibrous.

*Root development.*—Roots initiate in about 2 weeks and fully develop in about 3 months in a 4-liter container.

*Propagation.*—Softwood stem cuttings and tissue culture.

*Growth rate.*—Moderately vigorous.

Stem description:

*Shape.*—Round.

*Stem color.*—166A to 166B, under side strongly tinged 146B to 146C.

*Stem size.*—An average of 46.4 cm in length and 8 mm in diameter.

*Stem surface.*—Glabrous.

*Stem aspect.*—Upright, in an average angle of 45° (0°=vertical).

*Stem strength.*—Moderately strong.

*Branching.*—Moderately free branching, an average of 4 lateral branches.

*Internode.*—Average of 4.1 cm.

Foliage description:

*Leaf shape.*—Hastate to ovate.

*Leaf division.*—Simple.

*Leaf base.*—Hastate to reniform.

*Leaf apex.*—Long acuminate.

*Leaf venation.*—Pinnate, upper surface; 187A to 187B in color, lower surface; 153C and tinged 184A to 184B in color.

*Leaf margins.*—Irregular crenate, undulate.

*Leaf attachment.*—Petiolate.

*Leaf arrangement.*—Alternate.

*Leaf orientation.*—Held slightly pendulant.

*Leaf surface.*—Both surfaces glabrous, upper surface; satiny, lower surface; matte.

*Leaf color.*—Young leaves upper surface; 143A to 143B, young leaves lower surface; 143B to 143C, mature leaves upper surface; A blend of N187A, 200A, 200B, 147A and 143B, mature leaves lower surface; a blend of 146B and 147B.

*Leaf size.*—Average of 17.4 cm in length, and 12.2 cm in width.

*Leaf quantity.*—Average of 12 leaves per lateral branch.

*Petioles.*—Average of 9 cm in length, 5 mm in width, and 3.5 mm in height, upper surface color; slightly darker and than 183A in color, lower surface color; a color between 177A and 200D, surface glabrous.

Flower description:

*Inflorescence type.*—Flowers are solitary in leaf axils.

*Lastingness of flowers.*—Average of 4 days, self cleaning.

*Flower size.*—An average of 13.6 cm in depth and 6.4 cm in diameter (grown in a 23-cm container), up to 25 cm in spread when grown in a larger container or in the landscape.

*Flower fragrance.*—None.

*Flower shape.*—Rotate, typical *Hibiscus* shape.

*Flower number.*—Average of 1 per lateral stem.

*Flower aspect.*—Outward to slightly upright.

*Flower bud.*—Ovate in shape, an average of 4.2 cm in length and 3.3 cm in width, color; between 143B and 144A, tinged 178A and between 164B to 164C at the top, surface glabrous.

*Flower attachment.*—Petiolate.

*Petal number.*—5.

*Petal shape.*—Reniform to orbicular.

*Petal color.*—Upper surface when opening; 73D, veins N57A to N57B, base in between N45A and 53A, lower surface when opening; 73D, veins 155A, upper surface when fully open; 69C to 69D, veins N57B, base in between N45A and 53A, lower surface when fully open; 69C to 69D, veins 155A, petal color fading to 63B, base N79A.

*Petal surface.*—Both surfaces glabrous, upper side glossy, lower side matte.

*Petal margins.*—Slightly undulate, overlapping.

*Petal apex.*—Rounded.

*Petal size.*—Average of 8 cm in length and 10.1 cm in width.

*Petaloids.*—Not present.

*Sepal number.*—5.

*Sepal shape.*—Ovate.

*Sepal margin.*—Entire.

*Sepal size.*—Average of 4.3 cm in length and 2.2 cm in width (measured at the base of the free part).

*Sepal aspect.*—Rotate, lower 46.5% fused.

*Sepal surface.*—Both surfaces glabrous and matte.

*Sepal apex.*—Broad acute.

*Sepal base.*—Broadly cuneate and fused.

*Sepal color.*—Young upper surface; 145A, young lower surface; 143B to 144A, tinged 178A, mature upper surface; 145A, mature lower surface; 143B to 144A, tinged 178A at the top.

*Calyx.*—Rotate in shape, average of 3.6 cm in length and 5.1 cm in diameter.

*Pedicels.*—None.

*Peduncles.*—Average of 7.9 cm in length, 3 mm in diameter, glabrous surface, held at an average angle of 40° (0°=straight on top of lateral branch), moderately strong, color; upper side 175A, lower side 146C.

*Epicalyx.*—Comprised of an average of 17 bracteoles, linear in shape, curled upright, average of 3 mm in length and width, upper surface color 144B, lower surface color 144A, both surfaces are glabrous.

Reproductive organs:

*Gynoecium.*—1 pistil, average of 3.9 cm in length, stigmas; club-shaped, an average of 5 and 49D in color, style; 3.7 cm in length and NN155B in color, ovary; 145B in color and completely covered by the base of the style.

*Androecium.*—Stamens; average of 120, clustered and implanted in style, anthers; dorsifixed and orbicular in shape, 1 mm in length and 196B in color; filaments; 2 mm in length and 155A in color, pollen; moderate in quantity and 161A to 161B in color.

*Fruit/seeds.*—None observed to date.

It is claimed:

1. A new and distinct cultivar of *Hibiscus* plant named 'TAHI12' as herein illustrated and described.

* * * * *